United States Patent
Ren et al.

(10) Patent No.: US 11,352,463 B2
(45) Date of Patent: *Jun. 7, 2022

(54) BIO-BASED MEG AND POLYESTER COMPOSITIONS AND METHODS OF MAKING THE SAME

(71) Applicants: THE COCA-COLA COMPANY, Atlanta, GA (US); CHANGCHUN MEIHE SCIENCE AND TECHNOLOGY DEVELOPMENT CO., LTD., Jilin (CN)

(72) Inventors: Haiyu Ren, Atlanta, GA (US); Marlon Salvador Morales, Clemson, SC (US); Yi Yuan, Changchun (CN); Jing Liu, Changchun (CN); Hongbin Qi, Changchun (CN)

(73) Assignees: Changchun Meihe Science and Technology Development Co., LTD., Jilin (CN); The Coca-Cola Company, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/348,408

(22) PCT Filed: Nov. 9, 2017

(86) PCT No.: PCT/US2017/060807
§ 371 (c)(1),
(2) Date: May 8, 2019

(87) PCT Pub. No.: WO2018/089600
PCT Pub. Date: May 17, 2018

(65) Prior Publication Data
US 2019/0330417 A1   Oct. 31, 2019

(30) Foreign Application Priority Data

Nov. 9, 2016 (CN) .......................... 201610986991.4

(51) Int. Cl.
| | |
|---|---|
| C08G 63/183 | (2006.01) |
| B29C 49/00 | (2006.01) |
| B29C 49/08 | (2006.01) |
| C07C 31/20 | (2006.01) |
| B29K 67/00 | (2006.01) |
| B29L 31/00 | (2006.01) |

(52) U.S. Cl.
CPC ........ *C08G 63/183* (2013.01); *B29C 49/0005* (2013.01); *B29C 49/08* (2013.01); *C07C 31/202* (2013.01); *B29K 2067/003* (2013.01); *B29L 2031/7158* (2013.01); *C08G 2390/00* (2013.01)

(58) Field of Classification Search
USPC .......................................................... 528/298
See application file for complete search history.

(56) References Cited

U.S. PATENT DOCUMENTS

| | | | |
|---|---|---|---|
| 2008/0103340 A1* | 5/2008 | Binder | C07C 29/60 |
| | | | 568/863 |
| 2008/0275277 A1 | 11/2008 | Kalagias | |
| 2010/0019191 A1 | 1/2010 | Hoffer et al. | |
| 2010/0154376 A1* | 6/2010 | Nadkarni | D01F 6/84 |
| | | | 57/243 |
| 2014/0163195 A1 | 6/2014 | Berti et al. | |
| 2014/0197580 A1 | 7/2014 | Poulat | |
| 2020/0063294 A1* | 2/2020 | Moffitt | C08G 63/42 |

FOREIGN PATENT DOCUMENTS

| | | |
|---|---|---|
| AU | 2015201314 | 4/2015 |
| CN | 101525782 | 9/2009 |
| CN | 103668538 | 3/2014 |
| CN | 104418997 | 6/2016 |
| EP | 2684906 | 4/2016 |
| JP | 2014001257 | 1/2014 |
| WO | 2015028156 A1 | 3/2015 |
| WO | WO 2016/001169 | 1/2016 |

OTHER PUBLICATIONS

International Search Report and Written Opinion, PCT/US17/060807, 7 pages, Feb. 14, 2018.
Extended European Search Report for European Application No. 17869799.1, dated May 12, 2020.
Extended European Search Report for European Application No. 17869528.4, dated Jun. 4, 2020.
Xiao et al., Synthesis and Characterization of Poly(ethylene terephthalate) from Biomass-Based Ethylene Glycol: Effect of Miscellaneous Diols, Ind. Eng. Chem. Res. 2015, 54, 5862-5869.
Third Party Observations filed in European Patent Application No. 17869528.4, Dec. 23, 2021.
Third Party Observations filed in European Patent Application No. 17869799.1, Dec. 23, 2021.

* cited by examiner

*Primary Examiner* — Terressa Boykin
(74) *Attorney, Agent, or Firm* — King & Spalding

(57) ABSTRACT

Disclosed are bio-based mono-ethylene glycol (MEG) compositions containing from about 1 ppm to about 5000 ppm of at least one C3-C12 1,2-diol, bio-based polyester compositions made therefrom, and methods of making the same are disclosed. Preforms and blow-molded polyester containers prepared from the bio-based MEG and polyester are described.

13 Claims, 1 Drawing Sheet

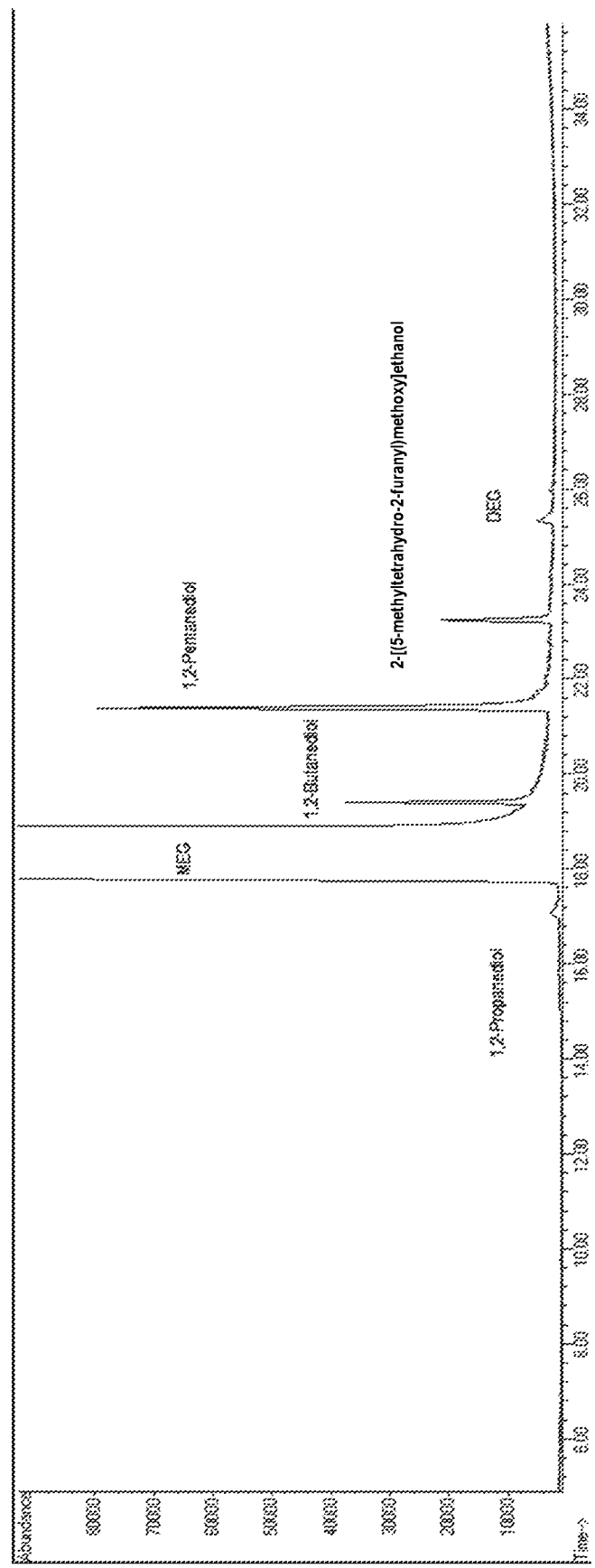

BIO-BASED MEG AND POLYESTER COMPOSITIONS AND METHODS OF MAKING THE SAME

CROSS-REFERENCE TO RELATED APPLICATIONS

This application is a 35 U.S.C. § 371 National stage application of International Patent Application No. PCT/US2017/060807, filed Nov. 9, 2017, which claims the benefit of priority to Chinese Patent Application No. 2016109869914, filed on Nov. 9, 2016, the entirety of each of which is hereby incorporated herein by reference.

FIELD OF THE DISCLOSURE

This disclosure relates to monoethylene glycol (MEG) compositions, and polyesters such as polyethylene terephthalate (PET), and methods of making the same and, more particularly, to bio-based MEG and polyester compositions and methods of making the same.

BACKGROUND

Polyesters such as polyethylene terephthalate are widely used for industrial and consumer applications, for example pipe, retail and pharmaceutical packaging, food and beverage packaging such as beverage bottles, toys, carpet, appliances and many other household items. Due to their excellent combination of clarity, mechanical, and gas barrier properties, polyethylene terephthalate and its co-polyesters (hereinafter referred to collectively as "PET") are particularly useful for fabricating beverage containers, such as bottles for carbonated soda drinks, still or carbonated water, fruit juice, and the like. Standard PET bottle production can involve, for example, the injection molding of a PET preform, followed by blow-molding or stretch blow-molding the perform to manufacture a PET bottle.

Conventional PET polyester is usually produced from the condensation reaction of terephthalic acid with monoethylene glycol (MEG), also referred to simply as ethylene glycol. Both of these PET precursors are normally derived from petrochemical sources. For example, terephthalic acid is generally formed by the oxidation of p-xylene and MEG is generally derived from the oxidation of ethylene, both of which are produced from petrochemicals.

Over time, consumer demand has increased for limiting the use of oil and petroleum-based products, including plastics, in consumer products, and preferences for more "natural" or plant-based or -derived products have expanded. To meet this consumer demand, there remains a need for improvements in the current polymerization processes to produce PET from plant-based sources. In particular, there is a need to produce PET precursors such as MEG entirely from biological or plant-based sources, rather than from traditional petroleum sources.

SUMMARY

This disclosure generally focuses on the monoethylene glycol (MEG) precursor for polyesters such as polyethylene terephthalate and its co-polyesters (PET), and provides generally for bio-based MEG, PET compositions made using bio-based PET, and methods of making the same, and bottles and containers made using the bio-based MEG and PET. The MEG disclosed herein can be used as a polyester precursor for any polyester that uses ethylene glycol as the diol precursor. Therefore, reference to PET throughout this specification should be viewed as exemplary, that is, this disclosure also provides for bio-based polyesters derived from MEG and terephthalic acid, furandicarboxylic acid, naphthalic acid, or any combinations thereof, such as isophthalic acid, 2,6-naphthalenedicarboxylic acid, 2-(2-carboxyphenyl)benzoic acid, or 2,5-furandicarboxylic acid, and copolyesters comprising combinations thereof. The resulting polyesters and co-polyesters can also be used in any polyester application such as films and containers, including containers such as bottles, drums, carafes, coolers, and the like. Surprisingly, it has been discovered that polyester bottles such as PET bottles made from bio-based MEG are significantly more transparent than polyester bottles made from petroleum-based MEG.

In one aspect, the monoethylene glycol (MEG) that is bio-based can be described according to the minor concentrations of the additional diol components, alcohol components, or other hydroxyl-containing components contained in the bio-based MEG. The additional diol components include, for example, 1,2-diols. One aspect of the disclosure relates to a bio-based MEG composition that includes monoethylene glycol (MEG) and at least one $C_3$-$C_{12}$ 1,2-diol, including $C_3$-$C_{12}$ 1,2-diols that can be linear, branched, or cyclic. A further aspect of the disclosure relates to a bio-based MEG composition comprising: monoethylene glycol (MEG); and from about 1 ppm to about 5000 ppm of at least one $C_3$-$C_{12}$ 1,2-diol, wherein the $C_3$-$C_{12}$ 1,2-diol is linear, branched, or cyclic.

Still a further aspect of the disclosure relates to a bio-based MEG composition comprising: monoethylene glycol (MEG); from about 1 ppm to about 5000 ppm of at least one $C_3$-$C_{12}$ 1,2-diol, wherein the $C_3$-$C_{12}$ 1, 2-diol is linear, branched, or cyclic; and an alcohol, particularly 2-[(5-methyltetrahydro-2-furanyl)methoxy]ethanol. In this aspect, the bio-based MEG can be described according to the presence of this particular alcohol.

Yet another aspect of the disclosure relates to a method of making a bio-based PET composition comprising the step of: reacting the MEG composition of any of the aspects described above with a diacid such as terephthalic acid. Finally, this disclosure provides for preforms made from the bio-based MEG and bio-based PET prepared therefrom, and further describes the containers and bottles made from these preforms.

BRIEF DESCRIPTION OF THE DRAWINGS

Advantages of the methods, processes and systems of the present disclosure may become apparent to one of skill in the art upon reading the following detailed description and upon reference to the drawings in which:

FIG. 1 is a gas chromatogram (FID detector) of a bio-based MEG composition produced according to an aspect of the present disclosure.

DETAILED DESCRIPTION

Several specific embodiments and/or aspects of the present disclosure are described herein. To provide a concise description of these embodiments, not all features of an actual implementation are necessarily described in the specification. It should be appreciated that in the development of any such actual implementation, as in any engineering or design project, numerous implementation-specific decisions are made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill in the art and having the benefit of this disclosure.

The Bio-Based MEG Composition

According to aspects of the present disclosure, bio-based MEG compositions and the PET derived therefrom can be produced from plant mass and in particular, the sugars contained therein. Suitable sugars include, but not limited to glucose, xylose, sucrose, fructose, and mixtures thereof. For example, sugar cane may be fermented using means known to one of ordinary skill in the art to produce ethanol and carbon dioxide. This ethanol may then be converted to ethylene using any of the known methods in the art, which may then be converted to MEG using standard processes, such as those used to convert petroleum-based ethylene to MEG. For example, a bio-based MEG composition may be produced by pyrolyzing a sugar to obtain a pyrolysis product composition; and hydrogenating the pyrolysis product composition in the presence of a catalyst and a solvent, under pressure, as discussed in detail in WO 2016/001169, which is hereby incorporated herein by reference.

Alternatively, a bio-based MEG composition may be produced in a continuous process whereby hydrogen, a carbohydrate source, and a liquid diluent can be continuously fed into a continuously stirred tank reactor (CSTR) wherein a catalyst system is present, and wherein the catalyst system comprises a tungsten compound and at least one hydrogenolysis metal selected from a Group 8, 9, or 10 metal, to achieve the reaction between the carbohydrate source and the hydrogen to form ethylene glycol. In this process, for example, at least one tungsten compound can be added to the CSTR continuously or periodically, as discussed in detail in WO 2016/114661, which is hereby incorporated herein by reference. In such a continuous process the tungsten compound may be selected from, for example, tungstic acid ($H_2WO_4$), ammonium tungstate, or ammonium metatungstate.

In a further aspect, the bio-based MEG can be prepared by from sucrose by hydrolyzing the sucrose to form a product stream containing glucose, fructose, and their derivatives, separating the reaction product stream into a fructose rich stream (including its derivatives) and a glucose rich stream (including its derivatives); and contacting the glucose rich stream with hydrogen in a reactor in the presence of a solvent and a catalyst system with catalytic hydrogenation abilities to produce a product stream comprising monoethylene glycol. An example of such as process is disclosed in U.S. Patent Publication No. 2016/0096789, which is hereby incorporated herein by reference.

In another aspect, plant mass such as sugar cane, corn wheat, cassava, agricultural waste, or wood chips may be used as a feed material and processed to help isolate the sugar and convert this sugar to MEG. For example, the sugar from a plant source can be fermented to generate ethanol and $CO_2$, and this bio-$CO_2$ can be converted to oxalic acid, which in turn can be reduced to MEG. Therefore, not only can the sugars derived from a plant source be used as bio-MEG precursors, but also the $CO_2$ derived from the fermentation process can be used as a bio-MEG precursor as well. Bio-MEG may also be produced by electrochemical routes from CO2.

While not intending to be bound by theory, it is believed that varying the source and relative amounts of plant mass used in the feed material may affect the types and contents of various sugars, thereby affecting the specific properties, such as specific by-products or impurities and their concentrations, of any MEG or PET composition produced therefrom. These MEG and PET compositions are suitable for a wide range of uses, including for use in fabricating beverage bottles.

It has been discovered that the bio-based MEG compositions described herein contain numerous impurities which generally are not present in standard petroleum-based MEG compositions, including numerous diols. Such diols are likely produced as by-products during the chemical reactions used to convert plant-based sugars to ethanol. Several of these impurities are shown in FIG. 1, which depicts a gas chromatogram of a MEG composition produced according to an aspect of the invention. This chromatogram identifies MEG, 1,2-propanediol, 1,2-butanediol, 1,2-pentanediol, diethylene glycol (DEG), and an unknown compound which has been identified as 2-[(5-methyltetrahydro-2-furanyl)methoxy]ethanol. The structure of 2-[(5-methyltetrahydro-2-furanyl)methoxy]ethanol is shown here.

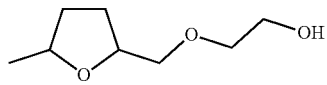

In some embodiments, each of the impurities listed above can be present in an amount of from about 1 ppm to about 5,000 ppm, for example about 1 ppm, about 100 ppm, about 500 ppm, about 1,000 ppm, about 2,000 ppm, about 3,000 ppm, about 4,000 ppm, or about 5,000 ppm. While not intending to be bound by theory, it is believed that the specific species and concentration of $C_3$-$C_{12}$ 1,2-diols present may be adjusted by adjusting the types and relative amounts of plant mass used as feed material to produce a bio-based MEG composition.

In embodiments of the present disclosure, a bio-based MEG composition may contain from about 1 ppm to about 5000 ppm of at least one $C_3$-$C_{12}$ 1,2-diol, wherein the $C_3$-$C_{12}$ 1, 2-diol is linear, branched, or cyclic, for example about 1 ppm, about 10 ppm, about 50 ppm, about 100 ppm, about 1000 ppm, about 2000 ppm, about 3000 ppm, about 4000 ppm, or about 5000 ppm of at least one $C_3$-$C_{12}$ 1,2-diol. In embodiments of the present disclosure, a bio-based MEG composition may further contain 2-[(5-methyltetrahydro-2-furanyl)methoxy]ethanol.

In some embodiments of the present disclosure, a bio-based MEG composition may contain from about 1 to about 100 ppm of 1,2-propanediol, or from about 1 to about 20 ppm of 1,2-propanediol. In some embodiments of the present disclosure, a bio-based MEG composition may contain from 1 to about 1000 1,2-butanediol, or from about 1 to about 80 ppm of 1,2, butanediol. In some embodiments of the present disclosure, a bio-based MEG composition may contain from about 1 to about 1000 ppm of 1,2-pentanediol, or from about 1 to about 500 ppm of 1,2-pentanediol. In some embodiments of the present disclosure, a bio-based MEG composition may contain from about 1 to about 1000 ppm of 1,2-hexanediol, or from about 1 to about 20 ppm of 1,2-hexanediol. In some embodiments of the present disclosure, a bio-based MEG composition may contain from about 1 to about 1000 ppm of 1,2-cyclopentanediol, or from about 1 to about 20 ppm of 1,2-cyclopentanediol. In some embodiments of the present disclosure, a bio-based MEG composition may contain from about 1 to about 1000 ppm of 2-[(5-methyltetrahydro-2-furanyl)methoxy]ethanol, or from about 1 to about 100 ppm of 2-[(5-methyltetrahydro-2-furanyl)methoxy]ethanol.

In some embodiments of the present disclosure, the bio-based MEG composition may contain any one of more of from about 1 to about 20 ppm of 1,2-propanediol, from about 1 to about 80 ppm of 1,2,-butanediol, from about 1 to about 500 ppm of 1,2-pentanediol, from about 1 to about 20 ppm 1,2-hexanediol, from about 1 to about 20 ppm of 1,2-cyclopentanediol, and from about 1 to about 100 ppm of 2-[(5-methyltetrahydro-2-furanyl)methoxy]ethanol. In some embodiments of the present disclosure, the bio-based MEG composition may contain any one of more of from about 5 to about 10 ppm of 1,2-propanediol, from about 30 to about 70 ppm of 1,2,-butanediol, from about 300 to about 450 ppm of 1,2-pentanediol, from about 5 to about 10 ppm 1,2-hexanediol, from about 5 to about 10 ppm of 1,2-cyclopentanediol, and from about 60 to about 80 ppm of 2-[(5-methyltetrahydro-2-furanyl)methoxy]ethanol.

The Bio-Based Polyester Composition

The bio-based MEG above may be reacted with terephthalic acid (PTA) to form the polyester PET, which is referred to herein as bio-PET or bio-polyester. In some embodiments, the bio-based MEG above may be reacted with any other aromatic diacids, including terephthalates, furanoates, naphthalates, and the like. For example, in some embodiments, the bio-based MEG above may be reacted with terephthalic acid, isophthalic acid, 2,6-naphtalenedicarboxylic acid, 2-(2-carboxyphenyl)benzoic acid, 2,5-furandicarboxylic acid, or any combinations thereof. In some embodiments, the bio-based MEG above may be reacted with a combination of aromatic diacids. While not intending to be bound by theory, it is believed that the specific combination and concentrations of $C_3$-$C_{12}$ 1,2-diol components derived from the bio-based MEG may reduce crystallization and crystallinity of the PET or other polymer produced from these MEG compositions, and may further improve PET or other polymer processability. That is, it is thought that these $C_3$-$C_{12}$ 1,2-diols may be incorporated as co-monomers which can lead to disruption of chain orientation or crystallinity development in the co-polyester PET resin as compared to PET resins without such $C_3$-$C_{12}$ 1,2-diols. That is, it is thought that these $C_3$-$C_{12}$ 1,2-diols in bio-based PET resins may disrupt the chain orientation or crystallinity development of the bio-based PET resin as compared to bio-based PET resins without such $C_3$-$C_{12}$ 1,2-diols. Moreover, these impurities may further improve the transparency and reflectivity and reduce the haze of a bottle produced from this PET. As used herein, "impurities" include any byproducts of the process used to produce the MEG. More transparent bottles are particularly desirable, as these align with consumer's preferences to be able to see the contents of a beverage bottle clearly through the bottle. The unexpected blend of MEG and minor diols provided by selecting the plant mass or carbohydrate from specific sources is thought to provide the improved results shown in the data of the Examples.

For example, consumers' perception of the transparency and clarity of bottles can be measured by the transmission haze percentage, which measures the scattering of light as it passes through a transparent material, as detailed in ASTM D1003. Surprisingly, in some embodiments of the present disclosure, the bio-based PET resin is clearer than a comparable petroleum-based PET resin. In other words, in some embodiments of the present disclosure, the transmission haze percentage of a bio-based PET resin is lower than the transmission haze percentage of a petroleum-based PET resin. For example, in one embodiment of the present disclosure, the transmission haze percentage of a bio-based PET resin is about 3.75% while the transmission haze percentage of a petroleum-based PET resin is about 4.2%. In some embodiments of the present disclosure, the transmission haze percentage of a bio-based PET resin is no more than about 10%. In some embodiments of the present disclosure, the transmission haze percentage of a bio-based PET resin is at least about 10%. In some embodiments, the transmission haze percentage of a bio-based PET resin may be about 10%, about 9%, about 8%, about 7%, about 6%, about 5%, about 4.75%, about 4.5%, about 4.25%, about 4%, about 3.75%, about 3.5%, about 3.25%, about 3%, about 2.75%, about 2.5%, about 2.25%, about 2%, about 1.75%, about 1.5%, about 1.25%, about 1%, about 0.75%, about 0.5%, or about 0.25%.

In some embodiments, the transmission haze percentage of a bio-based PET resin may be from about 20% to about 40% lower than the transmission haze percentage of a comparative oil-based PET resin. As used herein, a "comparative oil-based PET resin" is intended to refer to a PET resin which is identical in composition to the bio-based PET resin, except that the oil-based PET resin contains only oil-based MEG, and no bio-based MEG. For example, in some embodiments, the transmission haze percentage of a bio-based PET resin may be about 20% lower than the transmission haze percentage of a comparative oil-based PET resin, about 25% lower, about 30% lower, about 35% lower, about 40% lower, or any ranges therebetween.

The bio-based MEG disclosed herein also can be used as a polyester precursor for any polyester that uses ethylene glycol as the diol precursor, including for example, polyethylene naphthalate (PEN), polyethylene isophthalate, and the like. The bio-based MEG can further be used in any polyester co-polymers that may comprise some fraction of glycol (diol) modification, regardless of the whether the glycol used for modification is petroleum- or bio-based, and/or some fraction of diacid modification. For example, the bio-based MEG can be used in PET co-polymers having up to about 20 percent diacid modification, based on 100 mole percent diacid component in the bio-based PET. Diol (glycol) modification also occurs using bio-based MEG, but for the diol component, the co-diol can be from about 1 ppm to about 5000 ppm of at least one $C_3$-$C_{12}$ 1,2-diol, wherein the $C_3$-$C_{12}$ 1, 2-diol is linear, branched, or cyclic. That is, the co-diols are derived as a result of the production of bio-based MEG using the plant sources as described herein.

The polyester may be made using any suitable polycondensation catalysts; however, Applicants previously discovered that specific polycondensation catalysts may be particularly useful. For example, polycondensation catalysts such as those disclosed in U.S. Patent Publication No. 2006/0275568 can be used to make the bio-based PET. In one embodiment, the polyester may be made using at least one first polycondensation catalyst selected from the group consisting of metals in groups 3, 4, 13, and 14 of the Periodic Table. The polyester composition may comprise a catalyst residue remaining in the polyester from formation of the polyester and the catalyst residue may comprise at least a portion of the at least one first polycondensation catalyst. In some embodiments, the catalyst residue may be present in the polyester composition in an amount up to 250 ppm, and is preferably less.

If desired, the activity of the first polycondensation catalyst can be moderated using optional catalyst deactivating compounds, such as phosphorus containing compounds, to the polyester composition. The phosphorus containing compounds include both organic and inorganic compounds. Examples include but are not limited to phosphoric acid, polyphosphoric acid, and tris(2,4-di-t-butylphenyl) phosphite, tris monononylphenyl phosphite.

In other embodiments the bio-based PET composition may comprise a second polycondensation catalyst selected from the group consisting of cobalt, antimony, zinc, manganese, magnesium, cesium, calcium, and cadmium. Those skilled in the art should appreciate that the amount of the second polycondensation catalyst which is present in the polyester composition should be maintained below levels which may significantly lower the I.V. of the polyester composition below acceptable levels. Accordingly, in one embodiment the second polycondensation catalyst may be present in the polyester composition in an amount up to 3 ppm of the polyester composition. Specifically, the reactivity of traditional polycondensation catalysts such as cobalt, antimony, zinc, manganese, magnesium, cesium, calcium, calcium, and cadmium is not mitigated to the extent necessary to make use of the phosphorus-based deactivating agents a viable alternative compared to substantial reduction or elimination of the metal catalyst residues containing cobalt, antimony, zinc, manganese, magnesium, cesium, calcium, or cadmium.

In order to prepare container preforms and containers with adequate physical properties and an intrinsic viscosity (I.V. or IV) suitable for efficient molding of the preforms and blow molding of such preforms into containers, the polyester composition desirably has an I.V. of at least 0.60, more preferably from about 0.65 to about 1.0, and even more preferably from about 0.70 to about 0.86. The units for I.V. herein are all in dL/g measured according to ASTM D4603-96, in which the I.V. of bio-based PET based resin is measured at 30° C. with 0.5 weight percent concentration in a 60/40 (by weight) phenol/1,1,2,2-tetrachloroethane solution.

In some embodiments of the present disclosure, the bio-based PET composition has an average number of entanglements per molecule ($M_w/M_e$ or $M_n/M_e$) greater than the average number of entanglements per molecule of an analogous petroleum-based PET composition. For example, in some embodiments of the present disclosure, a bio-based PET composition has an average number of entanglements per molecule of 5.9 $M_n/M_e$ while a petroleum-based PET composition has an average number of entanglements per molecule of 5.7 $M_n/M_e$. In some embodiments of the present disclosure, the bio-based PET composition has an average number of entanglements per molecule of about 5.5 $M_n/M_e$, about 5.6 $M_n/M_e$, about 5.7 $M_n/M_e$, about 5.8 $M_w/M_e$, about 5.9 $M_n/M_e$, about 6.0 $M_n/M_e$, about 6.1 $M_n/M_e$, about 6.2 $M_n/M_e$, about 6.3 $M_n/M_e$, about 6.4 $M_n/M_e$, or about 6.5 $M_n/M_e$. In some embodiments of the present disclosure, a bio-based PET composition has an average number of entanglements per molecule of 11.1 $M_n/M_e$ while a petroleum-based PET composition has an average number of entanglements per molecule of 10.8 $M_n/M_e$. In some embodiments of the present disclosure, a bio-based PET composition has an average number of entanglements per molecule of 9.6 $M_n/M_e$ while a petroleum-based PET composition has an average number of entanglements per molecule of 7.5 $M_n/M_e$. In some embodiments of the present disclosure, a bio-based PET composition has an average number of entanglements per molecule of 18.4 $M_n/M_e$ while a petroleum-based PET composition has an average number of entanglements per molecule of 14.4 $M_n/M_e$. In some embodiments of the present disclosure, a bio-based PET composition has an average number of entanglements per molecule of about 9.0 $M_n/M_e$, about 9.1 $M_n/M_e$, about 9.2 $M_n/M_e$, about 9.3 $M_n/M_e$, about 9.4 $M_n/M_e$, about 9.5 $M_n/M_e$, about 9.6 $M_n/M_e$, about 9.7 $M_n/M_e$, about 9.8 $M_n/M_e$, about 9.9 $M_n/M_e$, about 10.0 $M_n/M_e$, about 10.1 $M_n/M_e$, about 10.2 $M_n/M_e$, about 10.3 $M_n/M_e$, about 10.4 $M_n/M_e$, about 10.5 $M_n/M_e$, about 10.6 $M_n/M_e$, about 10.7 $M_n/M_e$, about 10.8 $M_n/M_e$, about 10.9 $M_n/M_e$, about 11.0 $M_n/M_e$, about 11.1 $M_n/M_e$, about 11.2 $M_n/M_e$, about 11.3 $M_n/M_e$, about 11.4 $M_n/M_e$, about 11.5 $M_n/M_e$, about 11.6 $M_n/M_e$, about 11.7 $M_n/M_e$, about 11.8 $M_n/M_e$, about 11.9 $M_n/M_e$, or about 12.0 $M_n/M_e$.

In some embodiments of the present disclosure, the bio-based PET composition has a zero shear rate viscosity of from about 890 Pa·s to about 900 Pa·s. In some embodiments of the present disclosure, the bio-based PET composition has a zero shear rate viscosity of from about 900 Pa·s to about 1400 Pa·s. In some embodiments of the present disclosure, the bio-based PET composition has a zero shear rate viscosity of from about 1400 Pa·s to about 1700 Pa·s. In some embodiments of the present disclosure, the bio-based PET composition has a zero shear rate viscosity of from about 1500 Pa·s to about 1700 Pa·s. In some embodiments of the present disclosure, the bio-based PET composition has a zero shear rate viscosity of from about 1600 Pa·s to about 1700 Pa·s.

Examples

A bio-based MEG composition was prepared according to the following method. Gel permeation chromatography was used to generate the chromatogram shown in FIG. 1. Further analysis was able to identify the species and concentrations of impurities, as shown in Table 1 below.

TABLE 1

| Impurity | Concentration |
| --- | --- |
| 1,2-propanediol | <10 ppm |
| 1,2-butanediol | 71 ppm |
| 1,2-pentanediol | 418 ppm |
| valeroactone | <10 ppm |
| 2-[(5-methyltetrahydro-2-furanyl)methoxy]ethanol | 75 ppm |
| 1,2-hexanediol | <10 ppm |
| 1,2-cyclopentanediol | <10 ppm |
| Diethylene glycol (DEG) | <40 ppm |

While only the diols listed above were detected, without wishing to be bound by theory, it is believed that further diol impurities may be present, where these diols are a linear, branched, or cyclic $C_3$-$C_{12}$ 1,2-diol.

Then, this bio-based MEG was reacted with PTA produced from petroleum sources, although bio-based PTA could also be used according to methods which would be known to one of skill in the art. This PET was then used to create a stretch blow molded bottle, using methods known to those of skill in the art. Additionally, standard petroleum-based PET was used to make a stretch blow molded carbonated soda (CSD) bottle, using methods known to those of skill in the art. The transmission haze of each of these bottles was then measured, as shown in Table 2 below.

TABLE 2

| Sample | Transmission Haze % |
| --- | --- |
| PET CSD bottle made from petroleum-based MEG | 4.2 |
| PET CSD bottle made from bio-based MEG | 3.75 |

Surprisingly, as shown in Table 2, the PET bottle made from bio-based MEG had a significantly lower transmission haze percentage than that of the PET bottle made from petroleum-based MEG, meaning that the PET bottle from bio-based MEG was significantly more transparent than the PET bottle made from petroleum-based MEG.

Next, the Carreau-Yasuda parameters were used to calculate the plateau modulus and entanglement molecular weight for each sample, as would be understood by one of skill in the art. These calculated entanglement molecular weight values were then combined with the gel permeability chromatography molecular weight results to calculate the average entanglements per molecule, as shown in Table 3 below.

TABLE 3

| PET Sample | Intrinsic Viscosity (IV, dL/g) | Average No. of Entanglements per Molecule ($M_n/M_e$) | Average No. of Entanglements per Molecule ($M_w/M_e$) |
| --- | --- | --- | --- |
| Bio-based PET Water Bottle | 0.72 | 5.9 | 11.1 |
| Petroleum-based PET Water Bottle | 0.74 | 5.7 | 10.8 |
| Bio-based Carbonated Soft Drink Bottle | 0.83 | 9.6 | 18.4 |
| Petroleum-based Carbonated Soft Drink Bottle | 0.83 | 7.5 | 14.4 |

Surprisingly, the bio-based PET compositions exhibit a higher number of entanglements per molecule and a lower entanglement molecular weight than petroleum-based PET compositions. While not wishing to be bound by theory, it appears that the higher number of entanglements in the bio-based PET compositions helps to lock the molecular structure into place for longer, making molecular mobility in the amorphous regions more difficult, and slowing the cold crystallization process of the bottles, thereby keeping the transparency of the produced bottles for longer.

DEFINITIONS

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

The claim transitional phrases or terms are those described in MPEP 2111.03. The transitional term "comprising" is synonymous with "including," "containing," or "characterized by." However, absent an indication to the contrary, describing a process or composition as "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example a method can comprise several recited steps (and other non-recited steps) but utilize a catalyst system preparation consisting of specific steps but utilize a catalyst system comprising recited components and other non-recited components. While compositions and methods are described in terms of "comprising" various components or steps, the compositions and methods can also "consist essentially of" or "consist of" the various components or steps.

The terms "a," "an," and "the" are intended, unless specifically indicated otherwise or the context requires otherwise, to include plural alternatives, for example, at least one.

"Optional" or "optionally" means that the subsequently described event or circumstance can or cannot occur, and that the description includes instances where the event or circumstance occurs and instances where it does not.

The terms "configured for" or "adapted for" and similar language is used herein to reflect that the particular recited structure or procedure is used as described or claimed is designed, shaped, arranged, constructed, and/or tailored to effect the disclosed function, as would have been understood by the skilled person.

The term "bio-based" or simply "bio-" as used herein means at least mostly (>50 wt %) originating or produced from a biological material other than a petrochemical, such as plant mass, including but not limited to sugar cane, corn wheat, cassava, agricultural waste, wood chips, or any component thereof. As an example, when referring to a "bio-based MEG composition", Applicant's intent is that this refers to an MEG composition in which at least 50 wt % (and alternatively at least 75 wt % or at least 90 wt %) of the ethylene glycol in the composition is attributable to the biological material feedstock such as plant mass, or from sugars derived or isolated from plant mass (including but not limited to glucose, xylose, sucrose, fructose, or mixtures thereof) used to generate the MEG.

When describing a range of measurements such as temperatures, pressures, ratios and the like, it is the Applicant's intent to disclose every individual number that such a range could reasonably encompass, for example, every individual number that has at least one more significant figure than in the disclosed end points of the range. As an example, when referring to a concentration from about 1 ppm to about 20 ppm, Applicant's intent is that the disclosure of this range also discloses and is equivalent to the disclosure of about 1 ppm, about 2 ppm, about 3 ppm, about 4 ppm, about 5 ppm, about 6 ppm, about 7 ppm, about 8 ppm, about 9 ppm, about 10 ppm, about 11 ppm, about 12 ppm, about 13 ppm, about 14 ppm, about 15 ppm, about 16 ppm, about 17 ppm, about 18 ppm, about 19 ppm, and about 20 ppm. Applicant's intent is that these two methods of describing the range are interchangeable. Moreover, when a range of values is disclosed or claimed, Applicant also intends for the disclosure of a range to reflect, and be interchangeable with, disclosing any and all sub-ranges and combinations of sub-ranges encompassed therein. Accordingly, Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed herein, and that each value is also herein disclosed as "about" that particular value in addition to the value itself. In aspects, "about" can be used to mean within 10% of the recited value, within 5% of the recited value, within 2% of the recited value, or within 1% of the recited value.

Any headings that are employed herein are not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants reserve the right to proviso out any selection, feature, range, element, or aspect, for example, to limit the scope of any claim to account for a prior disclosure of which Applicants may be unaware.

What is claimed is:

1. A bio-based MEG composition comprising:
   monoethylene glycol (MEG); and
   from about 1 ppm to about 5000 ppm of 1,2-propanediol, 1,2-butanediol, 1,2-pentanediol, 1,2-hexanediol, 1,2-cyclopentanediol, and 2-[(5-methyltetrahydro-2-furanyl)methoxy]ethanol.

2. The bio-based MEG composition of claim 1, comprising the following:
   from about 1 to about 20 ppm of 1,2-propanediol;
   from about 1 to about 80 ppm of 1,2-butanediol;
   from about 1 to about 500 ppm of 1,2-pentanediol;
   from about 1 to about 20 ppm of 1,2-hexanediol;
   from about 1 to about 20 ppm of 1,2-cyclopentanediol; and
   from about 1 to about 100 ppm of 2-[(5-methyltetrahydro-2-furanyl)methoxy]ethanol.

3. The bio-based MEG composition of claim 1, comprising the following:
   from about 5 to about 10 ppm of 1,2-propanediol;
   from about 30 to about 70 ppm of 1,2-butanediol;
   from about 300 to about 450 ppm of 1,2-pentanediol;
   from about 5 to about 10 ppm of 1,2-hexanediol; from about 5 to about 10 ppm of 1,2-cyclopentanediol; and
   from about 60 to about 80 ppm of 2-[(5-methyltetrahydro-2-furanyl)methoxy] ethanol.

4. A method of making a bio-based PET composition comprising the step of:
   reacting the MEG composition of claim 1 with terephthalic acid, furandicarboxylic acid, naphthalic acid, isophthalic acid, 2,6-naphthalenedicarboxylic acid, 2-(2-carboxyphenyl)benzoic acid, 2,5-furandicarboxylic acid, or any combinations thereof.

5. A preform comprising a bio-based PET composition produced according to the method of claim 4.

6. A container comprising a bio-based PET composition produced according to the method of claim 4.

7. The container of claim 6, wherein the container is a bottle.

8. The container of claim 6, wherein the container is a carbonated soft drink bottle.

9. The container of claim 6, wherein the container has a transmission haze of at least about 2%.

10. A bio-based PET composition produced according to the method of claim 4.

11. The bio-based PET composition of claim 10, wherein the bio-based PET composition has an average entanglements per molecule (Mw/Me) greater than the average entanglements per molecule of an analogous oil-based PET composition.

12. The bio-based PET composition of claim 10, wherein the bio-based PET composition has a zero shear rate viscosity of from about 890 to about 1700 Pa·s.

13. The bio-based PET composition of claim 10, wherein the bio-based PET composition has an intrinsic viscosity of from about 0.6 dL/g to about 1.0 dL/g.

* * * * *